United States Patent [19]

Van Lier et al.

[11] Patent Number: 4,687,599
[45] Date of Patent: Aug. 18, 1987

[54] PERFUME COMPOSITIONS AND PERFUMED PRODUCTS WHICH CONTAIN ONE OR MORE 4,7-ALKADIENALS AS THE ESSENTIAL SUBSTANCE

[75] Inventors: Franciscus P. Van Lier; Leendert M. van der Linde; Antonius J. A. van der Weerdt, all of Huizen, Netherlands

[73] Assignee: Naarden International N.V., Naarden-Bussem, Netherlands

[21] Appl. No.: 767,490

[22] Filed: Aug. 20, 1985

[30] Foreign Application Priority Data

Aug. 23, 1984 [NL] Netherlands ......................... 8402579

[51] Int. Cl.$^4$ ................................................ A61K 7/46
[52] U.S. Cl. ....................................... 512/27; 568/448
[58] Field of Search ...................... 252/522 R; 568/448

[56] References Cited

U.S. PATENT DOCUMENTS 4,132,675 1/1979 Naf .................................. 252/522 R

FOREIGN PATENT DOCUMENTS 0554937 10/1974 Switzerland .

1034352 6/1966 United Kingdom .

OTHER PUBLICATIONS

J. P. Ward et al, "Synthesis of Some Aliphatic Dienals", Recueil des Travaux Chimiques des Pays-Bas, vol. 88, No. 2, pp. 177-184.

Primary Examiner—James H. Reamer
Attorney, Agent, or Firm—Brumbaugh, Graves, Donohue & Raymond

[57] ABSTRACT

Perfume compositions and perfumed products containing as perfume component one or more 4,7-alkadienals with the formula

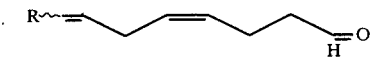

wherein R represents a straight-chain or branched-chain alkyl or alkenyl group containing 2–5 carbon atoms and wherein the 4–5 double bond has the cis-configuration and the 7–8 double bond can have the cis or trans configuration.

11 Claims, No Drawings

PERFUME COMPOSITIONS AND PERFUMED PRODUCTS WHICH CONTAIN ONE OR MORE 4,7-ALKADIENALS AS THE ESSENTIAL SUBSTANCE

The invention relates to perfume compositions which contain one or more 4,7-alkadienals as fragrance material and to products perfumed with one or more of these compounds or with the said compositions.

There is a permanent interest in the use of synthetic fragrance materials in perfumes and products to be perfumed such as cosmetics, soaps, detergents, household products etc. This interest is stimulated by the inadequate quantity, and often varying quality, of natural fragrance materials.

Surprisingly, it has now been found that 4,7-alkadienals having formula

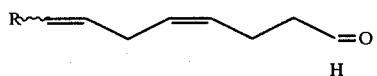

in which R represents a straight-chain or branched-chain alkyl or alkenyl group containing 2–5 carbon atoms and in which the 4–5 double bond has the cis configuration and the 7–8 double bond can have the cis or trans configuration, are valuable fragrance materials. Preference is given to compounds in which R represents a straight-chain alkyl or alkenyl group and the 7–8 double bond also has the cis configuration. More particularly, the compounds with formulae

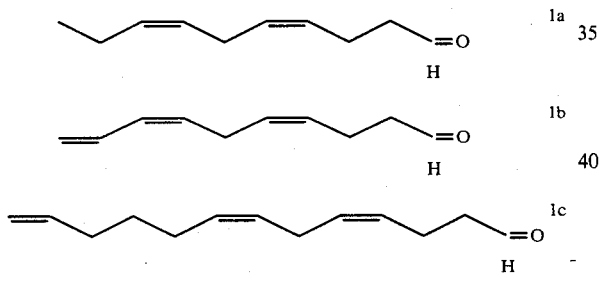

are preferred.

Various alkenals and alkadienals having 10 or more carbon atoms are known as fragrance materials or flavorings. Thus, in "Perfume and Flavor Chemicals", S. Arctander names 2,4-decadienal (No. 820) and 2-decenal (No. 842) without any reference to cis or trans configuration, and 8-, 9- and 10-undecenal (No. 3035 and 3036), of which 8- and 9-undecenal have the cis configuration. In U.S. Pat. No. 3,821,421 and Dutch Pat. No. 139,102 it is reported that both cis-4-decenal and cis, cis-4,7-tridecadienal and other polyunsaturated aldehydes containing 11–17 carbon atoms are suitable for imparting an aroma of chicken meat to foodstuffs. For this reason, however, it was not to be expected that these compounds would be suitable as a raw material for perfume compositions, in view of the fact that the odor of chicken meat is not valued in perfumery.

In Dutch Patent Application No. 71,17650 a method of synthesis is described for γ-δ-unsaturated carbonyl compounds including aldehydes. It is also reported therein that many of these compounds possess valuable organoleptic properties. As appears from claims 23, 24, 25 and 26 of this application, however, only compounds with a 2,4-diene system and/or an ester or keto group are in this instance involved.

In Dutch Patent Application No. 70,05187 and U.S. Pat. No. 3,920,752 it is reported that certain γ-δ-unsaturated aldehydes are valuable fragrance materials. From the structural formulae it appears, however, that in this instance only compounds with a trans γ-δ-double bond are meant.

None of these publications, therefore, gives any indication that in particular the 4,7-alkadienals according to the invention, in which at least the 4–5, and preferably also the 7–8, double bonds have the cis configuration, would be especially suitable as raw material for perfume compositions. Some of the compounds according to the invention are known as such from Rec. Trav. Chim. 88 (1969), pages 177–184. This publication, however, gives no data whatsoever about the organoleptic properties of these compounds.

The compounds according to the invention can be prepared by methods known per se for such compounds, for example those indicated in the reaction schemes reported below, wherein R has the meaning specified above. In the first of the examples below this synthesis has been worked out in detail for R=ethyl. The other compounds according to the invention can be prepared in a completely analogous manner.

The reaction according to Scheme II

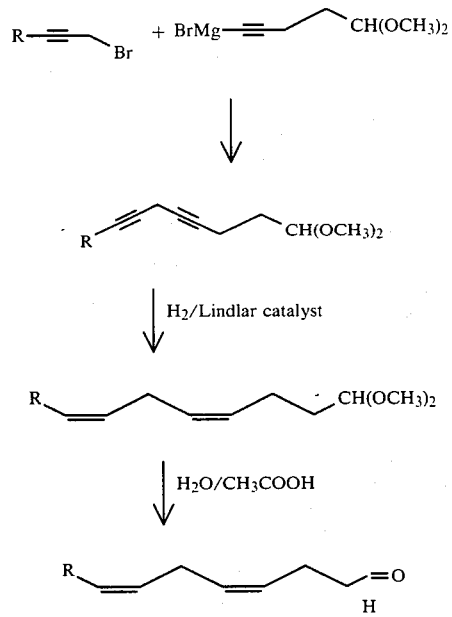

leads specifically to compounds with a cis 7–8 double bond, while the reaction according to Scheme I

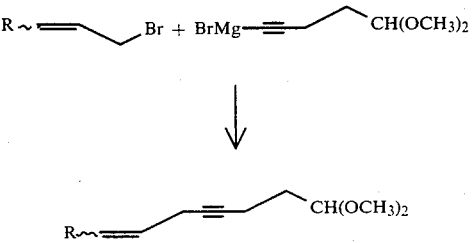

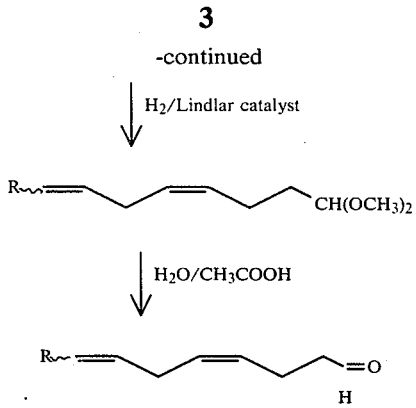

can lead to a cis or trans 7–8 double bond depending on the configuration of the starting material.

Alkadienals according to the invention are powerful fragrance materials which can be used with success as a raw material for perfume compositions and in all types of products to be perfumed, in order to impart to them various odor notes, for example of the green, fresh citrus, floral or aldehydic tupe.

The aldehydes in which R represents a non-branched alkyl or alkenyl group possess, moreover, a calamus-like odor and/or an odor reminiscent of orris root, while the compounds in which R represents an alkyl or alkenyl group containing 5 carbon atoms without a branched chain are notable for an odour of fresh flowers.

Here the expression "perfume composition" means a mixture of fragrance materials and possibly auxiliary substances, if desired dissolved in a suitable solvent or mixed with a powdery substrate which is used to impart a desired odor to the skin and/or all types of products. Examples of such products are: soaps, detergents, air fresheners, room sprays, pomanders, candles, cosmetics, such as creams, ointments, toilet waters, pre- and aftershave lotions, talcum powders, hair-care agents, body deodorants and anti-perspirants.

Fragrance materials and mixtures of fragrance materials which can be used in combination with the compounds according to the invention for manufacturing perfume compositions are, for example: natural products, such as essential oils, absolutes, resinoids, resins, concretes etc, but also synthetic fragrance materials such as hydrocarbons, alcohols, aldehydes, ketones, ethers, acids, esters, acetals, ketals, nitriles etc, including saturated and unsaturated compounds, aliphatic carbocyclic and heterocyclic compounds. Examples of fragrance materials which can be used in combination with the compounds according to the invention are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethyl-benzyl carbinol, trichloromethylphenyl carbinyl acetate, p-tert-butylcyclohexyl acetate, isononyl acetate, vetiveryl acetate, vetiverol, alpha-hexylcinnamaldehyde, 2-methyl-3-(p-tert-butylphenyl)-propanal, 2-methyl-3-(p-isopropylphenyl)-propanal, 3-(p-tert-butylphenyl)-propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decen-1-ol, phenoxyethylisobutyrate, phenylacetaldehydedimethylacetal, phenylacetaldehyde-diethylacetal, geranylnitrile, citronellylnitrile, cedrylacetate, 3-isocamphylcyclohexanol, cedrylmethyl ether, isolongifolanone, aubepinitrile, aubepine, heliotripine, coumarin, eugenol, vanillin, diphenyl oxide, hydroxycitronellal, ionones, methylionones, isomethylionones, irones, cis-3-hexenol and esters of the latter, indian-musks substances, tetraline-musks substances, isochromane-musks substances, macrocyclic ketones, macrolactone-musks substances, ethylene brassylate, aromatic nitromusks substances.

Auxiliary substances and solvents which can be used in perfume compositions which contain compounds according to the invention are, for example: ethanol, isopropanol, diethyleneglycolmonoethyl ether, diethylphthalate etc.

The quantities in which the compounds according to the invention can be used in perfume compositions or in products to be perfumed can vary within wide limits and depend inter alia on the nature of the product in which the fragrance material is used, on the nature and quantity of the other components in the perfume composition and on the odor effect which is aimed at. It is therefore only possible to specify very rough limits, which, however, provide sufficient information for the specialist to be able to use the compounds according to the invention independently. In most cases a quantity of only 10 ppm in a perfume composition will already be sufficient to obtain a clearly perceptible odor effect. On the other hand, to achieve special odor effects it is possible to use quantities of 5000 ppm or even more in a composition. In products perfumed with such compositions these concentrations are proportionately lower, depending on the quantity of composition used in the product.

The following examples are only to illustrate the preparation and use of the compounds according to the invention. The invention is not limited thereto.

EXAMPLE 1

Preparation of cis,cis-4,7-decadienal (according to Scheme II)

(A) Preparation of 1-bromo-2-pentyne

To a suspension of 1.2 mol of lithium amide in liquid NH$_3$ 34 g of propargyl alcohol (0.6 mol) were added in the course of 20 min. Subsequently, 94 g (0.6 mol) of ethyl iodide were added and then stirred for approx. 2 hours. The NH$_3$ was then allowed to evaporate and a saturated salt solution was added. The mixture was extracted with ether, the ether layers were combined, dried and concentrated by evaporation. The residue was purified by distillation. Approx. 12 g of 2-pentyn-1-ol were obtained.

This was dissolved in 20 ml of dry ether and 0.2 g of pyridine. 13 g of PBr$_3$ were added in approx. 30 minutes. Subsequently, the reaction mixture was heated under reflux for a further two hours and thereafter poured onto ice. The layers were separated and the organic layer dried and concentrated by evaporation. The residue was distilled under reduced pressure and 10 g of 1-bromo-2-pentyne were obtained.

(B) 1,1-dimethoxy-pent-4-yn-5-yl magnesium bromide was prepared in situ from ethyl magnesium bromide and 1,1-dimethoxy-4-pentyne. The latter was prepared as follows:

To an equivalent quantity of lithium acetylide in liquid NH$_3$ 55 g (0.3 mol) of 1-bromo-3,3-dimethoxypropane were added in 30 minutes. Subsequently, stirring was continued for a further 2 hours, after which the NH$_3$ was allowed to evaporate and the residue was dissolved in a mixture of ice and water. The mixture was extracted with ether and the combined organic layers were dried and concentrated by evaporation. The residue was distilled under reduced pressure and 11.5 g of 1,1-dimethoxy-4-pentyne were obtained.

9.5 g of the latter were dissolved in 60 ml of dry tetrahydrofuran, after which a solution of 10 g of ethyl magnesium bromide in 45 ml of ether was added.

(C) To the solution obtained under (B) 50 mg of CuCl were added as a catalyst, followed by 10 g of 1-bromo-2-pentyne dissolved in 60 ml of tetrahydrofuran. The reaction mixture was stirred for a further 30 minutes, poured into 100 ml of saturated ammonium chloride solution and subsequently extracted with pentane. The organic layer was washed, dried and concentrated by evaporation. The residue was fractionated under reduced pressure and 7.5 g of 1,1-dimethoxy-4,7-decadiyne were obtained. This was dissolved in 75 ml of cyclohexane, 250 mg of Lindlar catalyst were added and the mixture hydrogenated at atmospheric pressure until the theoretically required quantity of H$_2$ had been absorbed. Subsequently, the catalyst was filtered off, the solution concentrated by evaporation and the residue distilled under reduced pressure. The 1,1-dimethoxycis,cis-4,7-decadiene obtained was dissolved in 60 ml of acetic acid in which 0.02% of p-toluene sulfonic acid had been dissolved. Subsequently, approximately 15 ml of water were added and the mixture stirred at room temperature for 5 hours. The reaction mixture was then diluted with 300 ml of water and extracted with pentane. The organic layer was first washed to neutrality with sodium bicarbonate solution and then washed with water, dried and concentrated by evaporation. The evaporation residue was fractionated under reduced pressure. In this process 4 g of cis,cis-4,7-decadienal were obtained, b.p.: 70°/0.4 kpa; n 23/D=1.4624.

EXAMPLE II

A perfume composition of the chamomile type for use in soap was prepared according to the recipe below:

| | |
|---|---|
| Amylbenzoate | 200 parts by weight |
| 2-Butyl-4,4,6-trimethyl-1,3-dioxane | 120 parts by weight |
| Benzyl salicylate | 100 parts by weight |
| Allyl heptylate | 90 parts by weight |
| Ho oil | 75 parts by weight |
| Rose oil | 55 parts by weight |
| Guaiac wood oil | 50 parts by weight |
| Allylcyclohexyl propionate | 45 parts by weight |
| Geranium oil | 45 parts by weight |
| Petit grain oil | 40 parts by weight |
| Coumarin | 30 parts by weight |
| Rosemary oil | 25 parts by weight |
| Cis,cis-4,7-decadienal, 1% solution | 25 parts by weight |
| in dipropyleneglycol | |
| Total | 900 parts by weight |

The same composition was prepared wherein cis,cis-4,7,9-decatrienal was used instead of cis,cis-4,7-decadienal.

Two types of perfumed toilet soap were prepared by mixing 10 g of each of the two compositions with 1 kg of white soap grains and 10 g of soap colourant in a soap mill. From the coloured and perfumed soap chips obtained in this way pieces of toilet soap were pressed in the usual way. The two types of toilet soap had a somewhat different but very pleasant chamomile odour.

EXAMPLE III

A perfume composition of the lily-of-the-valley type was prepared for use in shower and bath foam products according to the recipe below:

| | |
|---|---|
| Hydroxycitronellal | 325 parts by weight |
| Rodinol | 200 parts by weight |
| β-Phenylethanol | 100 parts by weight |
| Benzyl benzoate | 50 parts by weight |
| Linalool | 50 parts by weight |
| α-hexylcinnamaldehyde | 40 parts by weight |
| Indole* | 30 parts by weight |
| β-Phenylethylphenylacetate | 20 parts by weight |
| 2-methyl-3-(p-isopropylphenyl)-propanal | 20 parts by weight |
| 3-hexenylacetate cis/trans* | 20 parts by weight |
| Benzyl acetate | 10 parts by weight |
| 10-undecenal** | 10 parts by weight |
| Decanal** | 10 parts by weight |
| Phenylethyl isobutyrate | 10 parts by weight |
| cis,cis-4,7,12-tridecatrienal** | 5 parts by weight |
| Total | 900 parts by weight |

*10% solution in diethyleneglycol monoethyl ether
**1% solution in diethyleneglycol monoethyl ether

We claim:

1. A perfume composition comprising an effective odorant amount of at least one alkadienal selected from the group consisting of cis,cis-4,7-decadienal, cis,cis-4,7,9-decatrienal and cis,cis-4,7,12-tridecatrienal.

2. A perfume composition according to claim 1 comprising at least 10 ppm, by weight, of at least one alkadienal selected from the group consisting of cis,cis-4,7-decadienal, cis,cis-4,7,9-decatrienal and cis,cis-4,7,12-tridecatrional.

3. A perfume composition comprising at least 10 ppm, by weight, of cis,cis-4,7-decadienal.

4. A perfume composition comprising at least 10 ppm, by weight, of cis,cis-4,7,9-decatrienal.

5. A perfume composition comprising at least 10 ppm, by weight, of cis,cis-4,7,12-tridecatrienal.

6. A perfumed product comprising an effective odorant amount of at least one alkadienal selected from the group consisting of cis,cis-4,7-decadienal, cis,cis-4,7,9-decatrienal and cis,cis-4,7,12-tridecatrienal.

7. A perfumed product comprising an effective odorant amount of cis,cis-4,7-decadienal.

8. A perfumed product comprising an effective odorant amount of cis,cis-4,7,9-decatrienal.

9. A perfumed product comprising an effective odorant amount of cis,cis-4,7,12-tridecatrienal.

10. Cis,cis-4,7,9-decatrienal.

11. Cis,cis-4,7,12-tridecatrienal.

* * * * *